United States Patent [19]

Picha

[11] Patent Number: 5,002,572
[45] Date of Patent: Mar. 26, 1991

[54] BIOLOGICAL IMPLANT WITH TEXTURED SURFACE

[76] Inventor: George J. Picha, 6554 Beechwood Dr., Independence, Ohio 44131

[21] Appl. No.: 274,917

[22] Filed: Nov. 22, 1988

Related U.S. Application Data

[63] Continuation-in-part of Ser. No. 906,177, Sep. 11, 1986, abandoned.

[51] Int. Cl.$^5$ ............................................. A61F 2/02
[52] U.S. Cl. ....................................... 623/11; 623/66; 424/424; 424/486
[58] Field of Search ............... 424/424, 425, 484, 486; 623/66, 16, 11

[56] References Cited

U.S. PATENT DOCUMENTS

| | | | |
|---|---|---|---|
| 4,340,458 | 6/1982 | Lerner et al. | 204/195 R |
| 4,396,464 | 7/1983 | Giner et al. | 204/1 T |
| 4,673,409 | 6/1987 | Van Kampen | 623/16 X |

OTHER PUBLICATIONS

Picha, G. J., and D. F. Gibbons, "Final Report—The Effect of Controlled Surface Morphology on the Subcutaneous Tissue Response," NASA Report CF-165319, Grant NAG 3-12, Mar. 1981.

Picha, G. J. and D. J. Siedlak, "Ion-Beam Microtexturing of Biomaterials," MD & DI, pp. 39–42, Apr. 1984.

Powell, E. A., "Changes in the Subcutaneous Tissue Response Caused by Implant Compliance and Surface Morphology," Master's Thesis, Case Western Reserve University, May 1982.

*Primary Examiner*—Alan W. Cannon
*Attorney, Agent, or Firm*—Tilton, Fallon, Lungmus & Chestnut

[57] ABSTRACT

An implant for soft tisse (e.g., subcutaneous, perivascular, adipose), particularly a mass transfer device having a fluid diffusing or transmitting surface in contact with the soft tissue, in which the surface of the device in tissue contact is textured to provide a regular pattern of micropillars at least 100 microns in height with transverse dimensions and interpillar spacing each no greater than 5000 microns.

9 Claims, 3 Drawing Sheets

CLASSICAL IMPLANT TISSUE RESPONSE

BIOLOGICAL IMPLANT WITH TEXTURED SURFACE

RELATED APPLICATION

This application is a continuation-in-part of my copending application Ser. No. 906,177, filed Sep. 11, 1986, now abandoned.

BACKGROUND AND SUMMARY

It is known that the implantation of an article or material into soft tissue initiates a sequence of physiological events in which the body attempts to remove or isolate the foreign entity. Macrophages at the site endeavor to ingest the foreign body, in some cases coalescing to form multinuculated giant cells. The presence of an implant may lead to the formation of a collagen layer of increased density as part of the host's attempt to isolate the foreign body. Such layer is commonly referred to as the "fibrous capsule" and its formation is dependent on a multiplicity of factors including surgical procedure, implant shape and size, relative movement between the implant and surrounding tissue, and surface charge and morphology.

The "classical" tissue response, as it has come to be known, is depicted somewhat schematically in FIG. 1. That figure represents a typical histological section, taken through a tissue block removed at four weeks from a dorsal implant in a Sprague-Dawley rat, of a cast silicone rubber disc 10 approximately 1 centimeter in diameter and 0.1 centimeter in thickness. It is characterized by the presence of macrophages and multinucleated giant cells 11 adjacent to the polymer surface 10a, a relatively thick fibrous capsule 12 (an average of 106 microns measured in 20 rat implants), and a layer of fat cells 13 that contain a minimal number of blood vessels and capillaries 14. In addition, the vascularity is spaced a substantial distance from the implant surface 10a.

It has been observed by investigators that the surface morphology of an implant may alter this response, as where the surface is provided with a multiplicity of projections or micropillars. In such a case, the fibrous capsule covering the micropillars has been found to be notably thinner in comparison with a fibrous capsule extending over a smooth-surface implant of the same material. Micropillars have also been found to influence the density, vascularity, and cellularity of the capsule, with such alterations being thought dependent more on the height of the pillars (at least 100 microns) than on their width. Picha, G.J., and Gibbons, D.F., "Final Report of the Effect of Controlled Surface Morphology on the Subcutaneous Tissue Response," NASA Report CR-165319, Section III, p. 2, Mar. 1981.

One aspect of this invention lies in the discovery that the width of such pillars and the distance between them, and the site of implantation in soft tissue, are also of significance in achieving an implant that yields a "non-classical" tissue response, and further, that such a response is highly significant if the implant is a mass-transfer device such as, for example, a sensor or a drug infusion device. If the width and spacing of the micropillars are both below 5000 microns, preferably below 3000 microns, and if the pillars exceed 100 microns in height, then a number of phemomena are found to occur. The thickness of the fibrous capsule is less than it would otherwise be if the surface of the implant were smooth rather than textured, with the result that the apertured or membrane-covered micropillars may protrude through the fibrous capsule into the tissue layer containing fat cells and blood vessels. Also, surprisingly, an increase in the vascularity of the tissue layer occurs. Such increased vascularity in close proximity to the ends of the pillars improves mass transfer of circulating organic substances between the vasculature and the implant.

In brief, the mass-transfer device takes the form of a supporting member or substrate having a surface textured to define a regular array of micropillars and valleys, and either a thin continuous diffusion membrane of substantially uniform thickness covering the micropillars and valleys and conforming with the surface texture of the member or, alternatively, microscopic apertures formed in the ends of the pillars through which a drug solution is slowly discharged into the surrounding tissue. Each micropillar, whether membrane covered or not, has a height no less than 100 microns and a width no greater than 5000 microns, with adjacent micropillars of the array being spaced apart a distance no greater than 5000 microns.

The micropillars may be generally rectangular (square) in section, or may be cylindrical in shape in any case preferably having a width within the range of about 25 to 3000 microns and being spaced apart a distance within the range of about 25 to 3000 microns. Where the implant takes the form of a sensor, such as a blood glucose sensor, the member or substrate may be electrically conductive and include in its composition a material capable of catalyzing a reaction with a selected blood analyte diffusible through the continuous membrane cover. Alternatively, if the implant is a drug infusion device, then the member or substrate may provide a reservoir containing an aqueous solution of the therapeutic agent and a multiplicity of passages leading from the reservoir and terminating in discharge apertures at the ends of the pillars. The drug may be discharged into the soft tissue directly through such apertures or may diffuse through a continuous membrane extending over the pillars and conforming to the contour of such pillars and the valleys between them.

Other features, advantages, and objects of the invention will become more apparent from the specification and drawings.

DRAWINGS

FIG. 1, already identified, illustrates in magnified cross section what is known to be the classical soft tissue response to a smooth-surfaced implant.

DETAILED DESCRIPTION OF PREFERRED EMBODIMENTS

Figure 2:
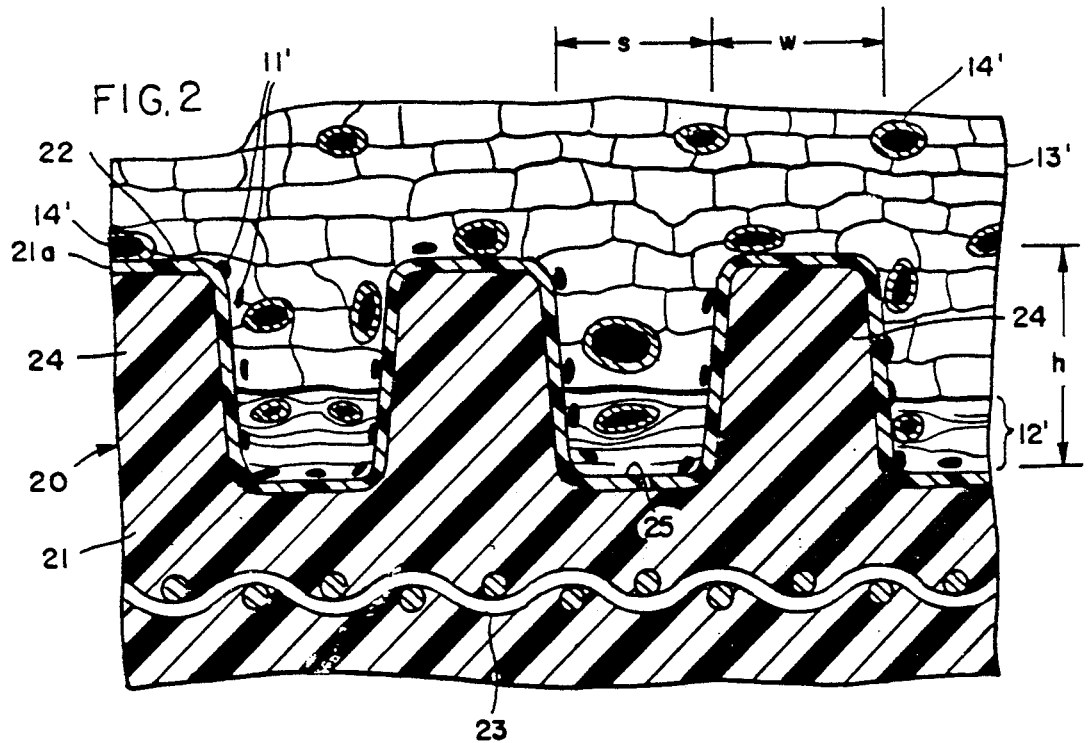
FIG. 2 is a magnified cross sectional view similar to FIG. 1 but illustrating a "non-classical" tissue response to a textured membrane-covered implant embodying this invention.

Referring to FIG. 2, the numeral 20 generally designates a mass-transfer device intended to be implanted in soft tissue, such as, adipose, subcutaneous, perivascular or intraperitoneal tissue. Device 20 is an implantable sensor, such as an electrocatalytic glucose sensor for continuously measuring blood glucose concentrations in diabetic patients and, with associated implanted electronic control and data transmission means (not shown), telemeters such information to an external receiver (not shown). The technology relating to the circuitry of such sensors is well known as disclosed, for example, in U.S. Pat. Nos. 4,340,458 and 4,396,464 and, since the present invention is concerned only with the surface morphology of the mass-transfer device and the advantages resulting therefrom, the circuitry and other details of the sensor will not be described herein.

Device 20 includes a substrate or member 21 having a textured surface covered by a thin continuous polymeric diffusion membrane 22. The polymeric substrate 21 contains throughout its composition a sufficient amount of finely-divided platinum black to provide a catalytic layer at the surface 21a of the substrate and to render the bulk of that substrate electrically conductive. A conductor in the form of a platinum screen or mesh 23 is embedded in the substrate and serves as a current collector.

Figure 3:
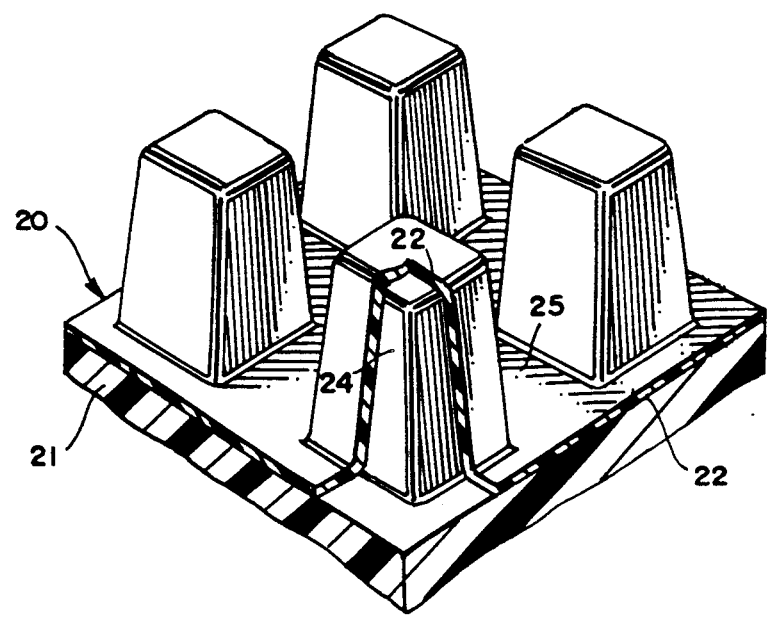
FIG. 3 is a fragmentary and greatly enlarged perspective view, partly in section, illustrating the micropillar structure of the implant of FIG. 2.

One or more surfaces of the substrate or membrane-supporting member 21 are textured as shown in FIGS. 2 and 3 to define a regular array of micropillars 24 with valleys or depressions 25 therebetween. Membrane 22 covers the micropillars and valleys and conforms with the surface contour of the substrate. The membrane-covered micropillars are of uniform dimensions and spacing, each having a height h of 100 microns or more, a width w no greater than 5000 microns and, preferably, within the range of 25 to 3000 microns, and a spacing s (or valley width) also no greater than 5000 microns and preferably in the range of 25 to 3000 microns. An upper limit for the height of the pillars has not been sharply defined, although particularly effective results have been achieved with micropillars having a height h within the range of 250 to 2000 microns.

As indicated in FIG. 3, the membrane-covered micropillars 24 are generally rectangular (square) in horizontal section and are arranged in rows extending at right angles to each other. The rectangular configuration, although advantageous from the standpoint of manufacturing the device, is not believed to be critical in terms of operation. A cylindrical shape, or other non-rectangular shape, might be used, as long as the width, height, and spacing fall within the limits described above. Also, any suitable method may be used to form the micropillars, although molding procedures have been found particularly effective. The mold from which the substrate, or the membrane, or both, are to be cast may be formed of metal, ceramic, or polymeric materials and its surface may be textured by means of laser etching techniques, ion milling, or chemical etching, all as well known in the art.

The substrate 21 may be formed from rigid, semirigid, or resilient materials depending at least in part on the purpose and operation of the mass-transfer device. As already indicated, biocompatible polymeric materials such as polyurethane, polymethylsiloxane, and co-polymers of HEMA and PMMA (polymethylmethacrylate) are suitable. Similarly, the selection of polymeric material for membrane 22 depends largely on the intended use of the mass-transfer device; in the case of a glucose sensor, cellulose acetate has been found suitable but any inert polymeric material having the desired mass transfer characteristics may be used.

Figure 1:
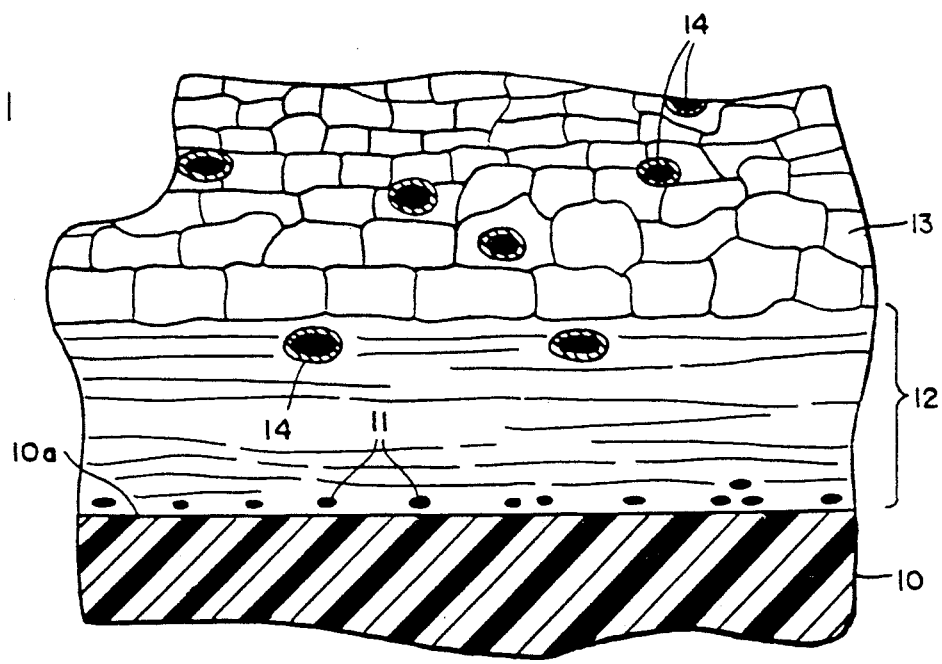

FIG. 2 illustrates what is termed a "non-classical" tissue response observed with microtextured implants (in rats) in which the micropillars measure approximately 500 microns in height and 250 microns in width, with an interpillar spacing of about 250 microns. Fibrous capsule 12' tends to be considerably thinner than the fibrous capsule 12 of the classical response depicted in FIG. 1 (for example, a mean thickness of about 78 microns in 20 implants) and, as shown, the fibrous capsule often tends to be located in the interstices between the pillars. The micropillars 24 therefore tend to protrude through the capsule into the cellular fat layer 13'. Macrophages and multinucleated giant cells 11' appear along and on top of the micropillars 24 as well as within valleys 25.

It has been found that when an implant is microtextured as shown in FIG. 2, the degree of vascularity increases and the thickness of the fibrous capsule decreases in comparison with the classical tissue response. The increased vascularity is represented by a greater number of vessels 14' (FIG. 2), but the precise reasons why angiogenesis should be enhanced by such microtexturing is not fully understood. It may be theorized that macrophages, being exposed to a greater surface area because of the texturing, become more active in eliciting those chemofactors that generate vascularity development. Whatever the reason, the increased vascularization, especially about the end portions of the micropillars protruding through fibrous capsule 12', plays an important role in improving the mass-transfer characteristics between the circulating blood and the polymer surface.

The reasons why microtexturing should result in fibrous capsule formation of reduced thickness are also not fully understood but, again, the result contributes in promoting mass transfer between the implant surface and tissue in contact with the fibrous capsule. The membrane-covered micropillars tend to protrude through the fibrous capsule 12' into the fatty and areolar tissue of greater vascularity. Particularly effective results have been observed for implantations in adipose tissue. For effective penetration of the fibrous capsule and surrounding tissue by the micropillars, the height h of those micropillars must not be less than, and should substantially exceed, 100 microns. The width of the pillars also plays a significant role, since widths in excess of those indicated may cause the micropillars to take on bulk surface characteristics with the formation of fibrous capsules over their tips.

The aspect ratio (width/height) of the micropillars may also be significant. An aspect ratio of 1:4 is believed particularly effective, especially with micropillars having widths falling within the range of 25 to 1000 microns, with a width of 500 microns being considered optimum.

Membrane 22 functions to present a biocompatible surface to the tissue and to exclude diffusible components that might "poison" the electrode while at the same time allowing facile mass transport of glucose and reaction products to and from the electrode and the circulating blood supply in vasculature 14'. In FIG. 2 only a single membrane 11' is shown; however, two or more such membranes having different diffusion characteristics may be employed to achieve the desired mass transfer characteristics for the sensor. In operation, the sensor is implanted in an appropriate site (subcutaneously or perivascularly) and electrically connected to distant auxiliary electrodes and electronics (not shown). After a period of healing and stabilization, the sensor is operated in a mode which selectively quantitates the glucose reaching the sensor surface. Consumption of the glucose by the sensor sets up a concentration gradient between the sensor surface and the circulating blood supply. Changes in the glucose concentration in the circulating blood are then indicated by the sensor with a lag time determined by the mass transfer resistance between the blood supply and the sensor (the lower the resistance, the shorter the lag time). The effect of microtexturing in reducing the mass transfer resistance therefore improves the sensitivity of the sensor and shortens the lag time for determining blood glucose transients.

Figure 4:
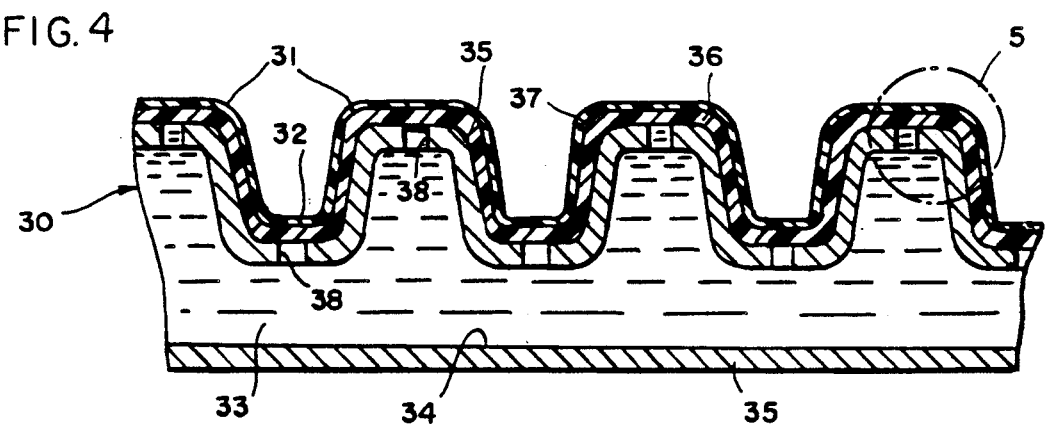
FIG. 4 is an enlarged fragmentary cross sectional view of a modified implant suitable for the delivery of therapeutic agents.
Figure 5:
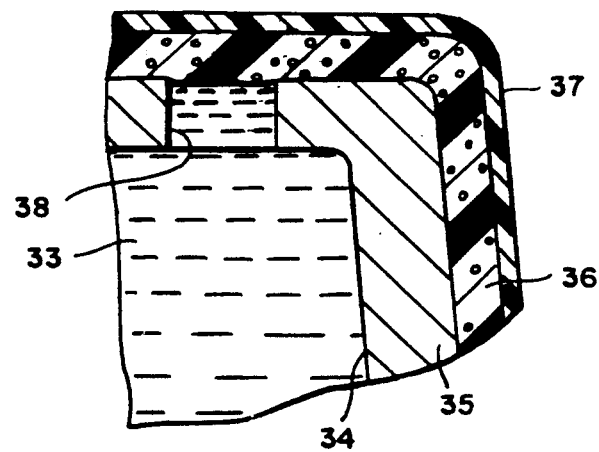
FIG. 5 is a further enlarged fragmentary sectional view of a portion of the implant device of FIG. 4 as indicated in that figure.

FIGS. 4 and 5 illustrate another mass-transfer device 30 which also has a textured surface characterized by a regular array of membrane-covered micropillars 31 and valleys 32. Although the proportions of the micropillars as shown in FIG. 4 differ from those depicted in FIG. 2, they nevertheless fall within the specified ranges and are, in general, of the same configuration as those of the first embodiment.

Device 30 is a microtextured implant for the delivery of a drug 33 contained in the reservoir 34 of hollow substrate or casing member 35. A bibulous film or layer 36 may be interposed between member 35 and diffusion membrane 37 for the purpose of dispersing the drug from reservoir 35 along the inside surface of membrane 37. Passages 38 extend through the wall of member 35 to permit such distribution, at least some of such passages being located at the ends of the micropillars of member 35.

Although such an implantable drug delivery device would be useful for administering any of a variety of drugs to the systemic circulation on a chronic or periodic basis, one clear example would be the chronic delivery of insulin to diabetics. The drug is periodically instilled into the reservoir through any suitable percutaneous means (not shown) in order to maintain a constant supply or to provide a bolus of a relatively high dose in order to respond to a specific medical situation (e.g., for diabetics, a bolus of insulin to respond to hyperglycemia caused by ingestion of a large meal). The drug 33 diffuses from the bibulous film 35 through the diffusion membrane 37 and is absorbed into the adjacent vasculature and circulated in the blood supply (the vasculature and surrounding tissue are omitted for clarity of illustration but would be the same as shown in FIG. 2.) The driving force for this process is the concentration gradient for the drug established between the implant and the adjacent vasculature. The rate of drug delivery is determined by the mass transfer resistance and the concentration of drug at the implant surface. Since microtexturing as specified herein reduces tissue mass transfer resistance, the rate of drug adsorption is enhanced. That rate can of course be modulated by selecting a diffusion membrane of the desired mass transfer resistance or by adjusting the concentration of the drug contained in the reservoir.

The thickness of the polymeric diffusion membrane (22, 37), as well as its composition will vary depending on the blood analyte to be sensed or the drug (or other therapeutic agent) to be delivered. In general, it is believed that such a membrane should have a thickness within the general range of 0.05 to 200 microns.

Figure 6:
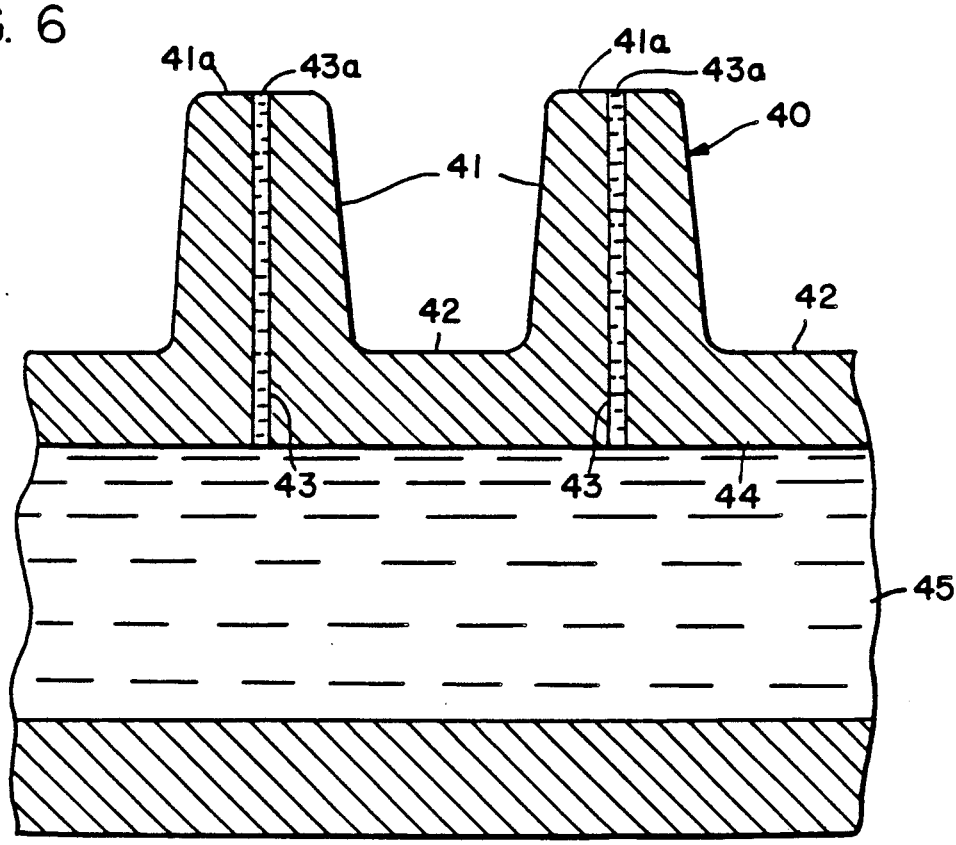
FIG. 6 is an enlarged fragmentary sectional view of an implant device constituting a further embodiment of this invention.

FIG. 6 depicts a further embodiment of the invention in which the drug delivery device 40 has a textured surface characterized by a regular array of micropillars 41 and valleys 42 falling within the dimensional ranges previously given. Unlike device 30, however, device 40 omits diffusion membrane 37 and bibulous layer 36. Passages 43 extend through the micropillars 41 from reservoir 44 to apertures 43a at the distal ends 41a of the micropillars. The passages may be of any size selected to permit the flow of therapeutic agent or drug 45 from the reservoir 44 to the surrounding tissue with the tissue itself serving as a diffusion membrane for the drug. Passage diameters within the range of 37 to 250 microns have been found effective, but other passage diameters may be suitable.

While in the foregoing I have disclosed embodiments of the invention in considerable detail for purposes of illustration, it will be understood by those skilled in the art that many of these details may be varied without departing from the spirit and scope of the invention.

I claim:

1. A mass transfer device for implantation in soft tissue, said device including a supporting member having an outer surface textured to define a regular array of micropillars with valleys therebetween, said textured surface comprising means for minimizing fibrous capsule formation and promoting mass transfer in soft tissue in the form of each of said micropillars having a height no less than 100 microns and a width no greater than 5000 microns, with adjacent micropillars in said array being spaced apart a distance no greater than 5000 microns.

2. A mass transfer device for implantation in soft tissue, said device including a supporting member having an outer surface textured to define a regular array of micropillars with valleys therebetween, each o said micropillars having a height no less than 100 microns and a width no greater than 5000 microns, with adjacent micropillars in said array being spaced apart a distance no greater than 5000 microns, and a thin diffusion membrane covering said micropillars and valleys and conforming with the surface contour of said member, said member being electrically conductive and including in its composition of catalyst capable of catalyzing a reaction with a selected blood analyte diffusible through said membrane.

3. A mass transfer device for implantation in soft tissue, said device including a supporting member having an outer surface textured to define a regular array of micropillars with valleys therebetween, said of said micropillars having a a height no less than 100 microns and a width no greater than 5000 microns, with adjacent micropillars in said array being spaced apart a distance no greater than 5000 microns, said member including a reservoir for containing an aqueous solution of a therapeutic agent and a multiplicity of passages extending from said reservoir through said micropillars to the ends thereof, and a thin diffusion membrane covering said micropillars and valleys and conforming with the surface contour of said member.

4. A mass transfer device for implantation in soft tissue, said device including a supporting member having an outer surface textured to define a regular array of micropillars with valleys therebetween, each of said micropillars having a height no less than 100 microns and width no greater than 5000 microns, with adjacent micropillars in said array being spaced apart a distance no greater than 5000 microns, said member including a reservoir for containing an aqueous solution of a therapeutic agent and a multiplicity of passages extending from said reservoir to discharge apertures at the ends of said micropillars.

5. The mass transfer device of claims 2, 3, or 4 in which said spacing falls within the range of 25 to 3000 microns.

6. The mass transfer device of claims 2, 3, or 4 in which said width falls within the range of 25 to 3000 microns.

7. The mass transfer device of claims 2 or 3 in which said diffusion membrane is a polymeric membrane of substantially uniform thickness.

8. The mass transfer device of claim 7 in which said thickness falls within the range of about 0.05 to 200 microns.

9. The mass transfer device of claims 2, 3, or 4 in which the width/height aspect ratio of each micropillar is about 1:4.

* * * * *

UNITED STATES PATENT AND TRADEMARK OFFICE
CERTIFICATE OF CORRECTION

PATENT NO. : 5,002,572

DATED : March 26, 1991

INVENTOR(S) : George J. Picha

It is certified that error appears in the above-identified patent and that said Letters Patent is hereby corrected as shown below:

Column 6, line 39, Cancel "o" and substitute "of"; line 53, cancel "said" (first instance) and substitute "each"; line 54, cancel "a" (first instance)

Signed and Sealed this

Eighth Day of September, 1992

Attest:

DOUGLAS B. COMER

*Attesting Officer*  *Acting Commissioner of Patents and Trademarks*